United States Patent [19]

Ghirga et al.

[11] 4,324,941

[45] Apr. 13, 1982

[54] PROCESS FOR THE PRODUCTION OF CUMENE

[75] Inventors: Marcello Ghirga, Bresso; Luigi Valtorta, Desio; Benedetto Calcagno, Milan, all of Italy

[73] Assignee: Euteco Impianti S.p.A., Milan, Italy

[21] Appl. No.: 225,220

[22] Filed: Jan. 15, 1981

[51] Int. Cl.³ .............................................. C07C 2/68
[52] U.S. Cl. ................................................... 585/466
[58] Field of Search ........................................ 585/466

[56] References Cited

U.S. PATENT DOCUMENTS

| | | | |
|---|---|---|---|
| 2,120,702 | 6/1938 | Ipatieff et al. | 585/529 |
| 2,613,188 | 10/1952 | Mavity | 585/466 |
| 3,813,451 | 5/1974 | Canfield et al. | 585/466 |
| 4,051,191 | 9/1977 | Ward | 585/466 |
| 4,108,914 | 8/1978 | Gewartowski | 585/466 |

*Primary Examiner*—Curtis R. Davis
*Attorney, Agent, or Firm*—Sughrue, Mion, Zinn, Macpeak and Seas

[57] ABSTRACT

Cumene is prepared by alkylation of benzene with propylene in the presence of a solid phosphoric acid catalyst in a continuous process by delivering liquid benzene and liquid propylene in a molar ratio lower than 6:1, to a liquid reaction medium consisting essentially of benzene and cumene and containing the catalyst, while maintaining the temperature and composition of said medium substantially uniform in each point, operating at 170°–280° C. and in the liquid phase, and with a contact time higher than about 0.4 hours, expressed as the ratio between volume of catalyst and hourly volume of reagents fed in.

10 Claims, No Drawings

PROCESS FOR THE PRODUCTION OF CUMENE

The present invention relates to an improved process for the production of cumene by the alkylation of benzene with propylene.

Cumene (or isopropylbenzene) is a valuable product, generally used as an intermediate in the synthesis of other compounds, especially phenol and acetone, via cumene hydroperoxide.

In the known art, the alkylation of benzene with propylene is carried out either in the gaseous or in the liquid phase in the presence of suitable catalysts, as described by S. H. McAllister et al in "Chemical Engineering Progress" Vol. 43, No. 4 (1947), at pages 189–196. The catalysts generally used are based on solid phosphoric acid, described for example in British Patent No. 863,539 and in U.S. Pat. Nos. 2,120,702 and 2,613,188, as well as in the article mentioned above.

In the known industrial processes, liquid benzene and liquid propylene are usually fed to a reactor which contains the catalyst in the form of one or more fixed beds. Moreover, in order to minimize the formation of poly-isopropylbenzene by-products (di-isopropylbenzene and tri-isopropylbenzene), a large excess of benzene with respect to the propylene is usually maintained in the feed, the benzene/propylene molar ratio being of the order of 6:1 to 10:1. The excess of benzene also serves to reduce the formation of propylene oligomers, such as the dimers and trimers.

In the processes described, given the exothermal nature of the reaction, hot points readily form in the catalytic bed giving rise to the formation of a gaseous phase with a high concentration of propylene, which promotes the formation of by-products such as polyalkylbenzenes and, particularly, propylene oligomers. Attempts have been made in the past to overcome this drawback by arranging the catalyst in several successive fixed beds and passing a cooling fluid between each pair of contiguous beds, as described, for example, in U.S. Pat. No. 3,813,451. This expedient does not, however, result in the complete elimination of the hot points in the catalytic beds.

An object of the present invention is to produce cumene using a low benzene/propylene ratio and with slight formation of by-products, in a medium in which the temperature is readily controllable. The use of low ratios between benzene and propylene results in a considerable saving of energy as well as better output, while the slight formation of by-products shows that there is a high selectivity towards the formation of the desired reaction product. Moreover, the ready controllability of the temperature improves the general course of the process for the preparation of cumene.

These desirable results are obtained according to the present invention by reacting benzene with propylene in a liquid reaction medium containing the solid phosphoric acid catalyst, using a continuous process and relatively high residence times, the temperature and the composition of said reaction medium being uniform or substantially uniform in each point.

More particularly, according to the present invention:

Benzene and propylene are continuously fed in the liquid form and in a molar ratio lower than 6:1, to a liquid reaction medium consisting essentially of cumene and benzene and containing the solid phosphoric acid catalyst, said medium being maintained homogeneous or substantially homogeneous in each point by efficient agitation, the reaction is carried out at a temperature of from 170° to 280° C. and under a pressure such as to maintain propylene in the liquid phase, with a contact time higher than about 0.4 hours, expressed as volume of catalyst per hourly volume of liquid reagents fed in, and with a conversion of propylene higher than about 60%, the liquid phase is continuously discharged and cumene is recovered from said liquid phase.

In a preferred embodiment, the catalyst is in the form of finely divided particles in suspension in the liquid reaction medium.

The present invention is essentially based on the observation that the contact time of the reagents under the reaction conditions has an influence on the amount of by-products, in the sense that said amount surprisingly decreases as the contact time is increased beyond the aforesaid threshold, when operating in a liquid medium containing in suspension the solid phosphoric acid catalyst, and when the composition and the temperature of said medium are maintained at uniform values by means of an efficient agitation of the mass, using for example mechanical agitators, a recycle of the liquid phase or the like. In other words, while the increase in residence time normally affords an increase in conversion accompanied by an undesired decrease in selectivity, the formation of by-products being promoted by the use of high residence times, by operating under the conditions of the invention the increase in residence time does afford a regular increase in conversion, but also, beyond a certain threshold, a regular increase in selectivity, as will be shown in the Examples. This eventually permits the amount of by-products to be reduced to very low values, while operating with low benzene/propylene molar ratios, and thus under economically favourable conditions.

In particular, as regards the feeding, the benzene/propylene molar ratio is conveniently maintained at a value not exceeding 4:1, and may reach values as low as 2:1. In a preferred embodiment, the benzene/propylene molar ratio is 3:1 or at least close to this value. It should be noted that, by using this last ratio in the process of the invention, typically 5 parts by weight of by-products, or even less, are obtained for every 95 parts by weight of cumene, depending on the contact time. Similar results are obtained in the conventional processes by using noticeably higher benzene/propylene molar ratios, and generally ratios of the order of 6:1–8:1.

The propylene used for the alkylation of the benzene may be pure or in mixture with inert substances, such as hydrocarbons non-reactive under the reaction conditions. In this last case, the reaction medium contains an inert compound, and this factor does not adversely affect the course of the alkylation reaction.

As mentioned above, the reagents are delivered to a liquid reaction medium consisting essentially of cumene and benzene, or more exactly of the products of the alkylation of benzene with propylene which essentially consist of benzene and cumene. The alkylation catalyst consisting of solid phosphoric acid is preferably suspended in said liquid medium in the form of small particles. Catalysts of this type are well known in the art and are generally prepared by mixing phosphoric acid in which phosphorus has a valency of 5, with a silicic material and heating the resulting mixture at elevated temperatures. A preferred catalyst for the purposes of the present invention is prepared from diatomite having a silica content of more than 70% by weight. More particularly, this support is heated at a temperature of the order of 250° C., until a specific surface area of about 10-30 m²/g is achieved. This support is then mixed with the commercial complex product known as polyphosphoric acid, having a $P_2O_5$ content of the order of 85% by weight. Conveniently, one part by weight of the support is mixed with two parts by weight of polyphosphoric acid, operating at ambient tmperature or a little above. The mixture thus obtained is calcined at a temperature of the order of 300° C. for a period generally greater than one hour.

In a preferred embodiment, before use, the catalyst is reduced to particles with a size of from 20 to 300 microns, preferably from 50 to 250 microns, and these particles are suspended in the liquid reaction medium. The optimum quantity of catalyst in the suspension is of the order of 10-20% by weight, although a wider range of concentration may be used, for example from 1 to 30% by weight.

The alkylation reaction is carried out at a temperature of from 170° to 280° C., the preferred range of temperatures being from 200° to 250° C. The operating pressure is such as to allow propylene to be maintained in the liquid phase in the reaction medium at the pre-chosen temperature. Usually, this object is achieved by using a pressure of the order of 15-50 kg/cm². One of the critical aspects of the process of the invention is the maintenance of the residence time under reaction conditions at values higher than about 0.4 hours, expressed as volume of catalyst/volume of liquid reagents fed in hourly. The upper limits of the residence time are not critical, and are essentially dictated by economical considerations, taking also into account the desired conversion of propylene. Generally, the residence time does not exceed values of the order of 3 hours, the preferred values being from 0.5 to 1 hour. By operating under the reaction conditions indicated above, the propylene conversion is generally higher than about 60% and may be complete, or substantially complete, depending on the residence time used.

A further important aspect of the process of the invention is the maintenance of the reaction medium as homogeneous as possible, or in other words with a composition and a temperature as uniform as possible in each point. This result may be achieved, in the case of the use of a suspension of catalyst in the liquid medium, by means of an efficient agitation of the mass, for example by carrying out the reaction in an autoclave fitted with agitators, or in a reactor with "gas-lift" type circulation in which the mass rises through a central tube and falls into a peripheral zone around the central tube. In the latter type of reactor the reagents are conveniently fed into the central zone at the bottom of the reactor.

The thermal effect of the reaction may readily be controlled by means of feeding in cool reagents, and it is also possible to make use of heat exchangers.

The reaction may be carried out in a single reactor, or in a plurality of reactors arranged in series. In each case, the liquid phase discharge from the reactor, or from the last reactor of the series, is submitted to conventional treatments to separate and recover cumene. Benzene and the possible unaltered propylene present in the reaction products are conveniently recycled.

By means of the process of the invention, it is possible to use the catalyst over long periods of time, while obtaining cumene outputs of the order of 2-5 kg per kg of catalyst and per hour.

The following experimental examples are illustrative and non-limitative for the invention.

EXAMPLES 1-13

There is used a reactor provided with an agitator, means for feeding in the reagents and means for discharging the reaction products. The reactor is also provided with heat exchange means.

The reactor is initially charged with a suspension of the catalyst, consisting of phosphoric acid supported on diatomite (as described above), in a mixture of benzene and cumene in a 3:1 weight ratio. The catalyst is in the form of particles with a size of from 50 to 250 microns.

The reaction is carried out continuously by delivering liquid benzene and liquid propylene to the reactor at an intermediate level thereof, and by discharging the reaction products through a filter arranged at the top of the reactor.

In Examples 1 to 13, the operating pressure was 35 kg/cm². The other conditions used are shown in Table 1. More particularly, the following parameters are shown in said Table:
reaction temperature in °C.,
quantity of catalyst in grams,
volume of the reactor in millimeters,
feed of reagents in ml/hour,
benzene/propylene molar ratio in the feed,
residence time in hours, expressed as the ratio between the volume in ml of catalyst used and the hourly volume in ml of reagents fed in. The density of the catalyst is 1.083 g/ml.

The reaction products continuously discharged from the reactor are separated and submitted to analysis. Under steady state conditions there are obtained the results shown in Table 1. More particularly, there are indicated in said Table:
the amounts of benzene, cumene, di-isopropylbenzenes and tri-isopropylbenzenes in weight percent in the liquid products discharged from the reactor,
the propylene conversion in percentage,
the amount of heavy by-products in parts by weight for each 1000 parts by weight of cumene.
Examples 1,2,4,5,10 and 11 are working examples.

TABLE 1

| Ex. | Temperature °C. | Catalyst (g) | vol. reactor (ml) | feed (ml/hr) | molar ratio benzene/propylene | contact time (hour) |
|---|---|---|---|---|---|---|
| 1 | 230 | 63.75 | 385 | 133 | 3 | 0.44 |
| 2 | 230 | 63.75 | 385 | 114 | 3 | 0.52 |
| 3 | 206 | 63.75 | 385 | 243 | 3 | 0.24 |
| 4 | 208 | 63.75 | 385 | 122 | 3 | 0.48 |
| 5 | 207 | 63.75 | 385 | 20 | 3 | 2.94 |
| 6 | 207 | 63.75 | 385 | 600 | 3 | 0.10 |
| 7 | 207 | 63.75 | 385 | 279 | 4 | 0.21 |
| 8 | 207 | 63.75 | 385 | 279 | 2 | 0.21 |
| 9 | 217 | 162.8 | 600 | 640 | 2.88 | 0.23 |

TABLE 1-continued

| | | | | | | |
|---|---|---|---|---|---|---|
| 10 | 204 | 162.8 | 600 | 310 | 2.88 | 0.48 |
| 11 | 203 | 162.8 | 600 | 150 | 2.93 | 1.00 |
| 12 | 210 | 162.8 | 600 | 3000 | 2.88 | 0.05 |
| 13 | 207 | 162.8 | 600 | 4500 | 2.88 | 0.03 |

| Ex. | benzene (%) | cumene (%) | di-isopropyl benzenes (%) | tri-isopropyl benzenes (%) | propylene conversion (%) | heavy products |
|---|---|---|---|---|---|---|
| 1 | 60.75 | 37.28 | 1.95 | 0.011 | 91.21 | 52.7 |
| 2 | 60.30 | 37.80 | 1.89 | 0.008 | 92.32 | 50.2 |
| 3 | 66.29 | 31.80 | 1.88 | 0.032 | 76.86 | 60.2 |
| 4 | 62.37 | 35.69 | 1.92 | 0.014 | 86.91 | 54.2 |
| 5 | 58.07 | 40.74 | 1.19 | 0.001 | 97.14 | 29.2 |
| 6 | 73.08 | 25.44 | 1.43 | 0.049 | 59.68 | 58.1 |
| 7 | 73.74 | 25.31 | 0.95 | 0.008 | 76.63 | 37.7 |
| 8 | 56.07 | 39.19 | 4.44 | 0.303 | 71.81 | 120.9 |
| 9 | 63.68 | 34.06 | 2.22 | 0.039 | 80.59 | 66.2 |
| 10 | 61.62 | 36.26 | 2.11 | 0.019 | 85.57 | 58.6 |
| 11 | 59.54 | 38.65 | 1.81 | 0.006 | 92.04 | 47.0 |
| 12 | 77.97 | 20.91 | 1.06 | 0.053 | 45.89 | 53.5 |
| 13 | 82.76 | 16.53 | 0.67 | 0.033 | 35.08 | 42.7 |

EXAMPLE 14

The test of Example 1 is repeated by using the following conditions:
temperature: 200° C.
catalyst: 67 g
volume of the reactor: 385 ml
benzene/propylene molar ratio in the feed: 3:1.

By varying the residence time, expressed in the manner already indicated, different values of the propylene conversion (in percent) and of the quantity of by-products (parts by weight for each 1000 parts by weight of cumene) are obtained. The results are shown in Table 2.

TABLE 2

| Residence time (hours) | Propylene conversion (%) | Heavy products |
|---|---|---|
| 0.13 | 60.8 | 56.6 |
| 0.25 | 74.1 | 59.0 |
| 0.50 | 84.9 | 54.2 |
| 0.75 | 89.2 | 49.4 |
| 1.00 | 91.6 | 45.4 |
| 1.25 | 93.1 | 42.3 |
| 2.50 | 96.4 | 32.7 |

EXAMPLE 15

The run of Example 14 is repeated by maintaining in the feed a molar ratio between benzene and propylene of 2:1. The results are shown in Table 3.

TABLE 3

| Residence time (hours) | Propylene conversion (%) | Heavy products |
|---|---|---|
| 0.13 | 57.7 | 106.3 |
| 0.25 | 71.5 | 117.0 |
| 0.50 | 82.2 | 114.6 |
| 0.75 | 86.9 | 108.3 |
| 1.00 | 89.6 | 102.2 |
| 1.25 | 91.4 | 96.9 |
| 2.50 | 95.3 | 78.9 |

We claim:
1. A process for producing cumene by alkylation of benzene with propylene in the presence of a solid phosphoric acid catalyst, which comprises:
 continuously delivering liquid benzene and liquid propylene in a benzene/propylene molar ratio lower than 6:1, to a liquid reaction medium consisting essentially of benzene and cumene and containing the solid phosphoric acid catalyst, the temperature and composition of said medium being maintained substantially uniform in each point by means of an efficient agitation;
 operating at a temperature of from 170° to 280° C., under a pressure such as to maintain propylene in the liquid phase, with a contact time higher than about 0.4 hours, expressed as the ratio between volume of catalyst and hourly volume of benzene and propylene fed in, and with a propylene conversion of at least about 60%; and
 discharging continuously a stream of liquid reaction medium and recovering cumene present in said stream.

2. The process of claim 1, wherein said benzene/propylene molar ratio is from 2:1 to 4:1.

3. The process of claim 1, wherein the catalyst is in the form of particles with a size of from 20 to 300 microns in suspension in the liquid reaction medium.

4. The process of claim 3, wherein said particles have a size of from 50 to 250 microns.

5. The process of claim 1, wherein the reaction medium contains from 1 to 30% by weight of catalyst.

6. The process of claim 1, wherein the reaction medium contains from 10 to 20% by weight of catalyst.

7. The process of claim 1, wherein the alkylation is carried out at a temperature of from 200° to 250° C.

8. The process of claim 1, wherein the operating pressure is from 15 to 50 Kg/cm$^2$.

9. The process of claim 1, wherein said contact time is from 0.4 to 3 hours.

10. The process of claim 1, wherein said contact time is from 0.5 to 1 hour.

* * * * *